US012333717B2

(12) United States Patent
Wang et al.

(10) Patent No.: US 12,333,717 B2
(45) Date of Patent: Jun. 17, 2025

(54) INFRARED IMAGE SEQUENCE-BASED SLEEP QUALITY EVALUATION SYSTEM AND METHOD COMPRISING PERFORMING EVALUATION BY A CLASSIFIER AND COUNTING THE SLEEP QUALITY EVALUATION RESULTS TO DETERMINE THE LARGEST NUMBER TO JUDGE GOOD OR POOR SLEEP QUALITY

(71) Applicant: SHENZHEN INSTITUTES OF ADVANCED TECHNOLOGY, Guangdong (CN)

(72) Inventors: Shuqiang Wang, Guangdong (CN); Senrong You, Guangdong (CN); Guobao Wu, Guangdong (CN); Yiqian Lu, Guangdong (CN); Fen Miao, Guangdong (CN); Chitang Zhang, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 329 days.

(21) Appl. No.: 17/786,840

(22) PCT Filed: Dec. 17, 2019

(86) PCT No.: PCT/CN2019/126038
§ 371 (c)(1),
(2) Date: Jun. 17, 2022

(87) PCT Pub. No.: WO2021/120007
PCT Pub. Date: Jun. 24, 2021

(65) Prior Publication Data
US 2023/0022206 A1    Jan. 26, 2023

(51) Int. Cl.
A61B 5/00          (2006.01)
A61B 5/08          (2006.01)
(Continued)

(52) U.S. Cl.
CPC .......... G06T 7/0012 (2013.01); A61B 5/0082 (2013.01); A61B 5/08 (2013.01);
(Continued)

(58) Field of Classification Search
CPC ....... A61B 5/0082; A61B 5/08; A61B 5/4815; A61B 5/7267; G06T 2207/10016;
(Continued)

(56) References Cited

U.S. PATENT DOCUMENTS 5,704,367 A    1/1998  Ishikawa et al.
10,729,332 B2 *  8/2020  Heneghan ............ A61B 5/0507
(Continued)

FOREIGN PATENT DOCUMENTS

CN    101489478 A  *  7/2009  .......... A61B 5/0205
CN    102973273 A      3/2013
(Continued)

OTHER PUBLICATIONS

"Global Second-order Pooling Convolutional Networks" Pub Date Jun. 16-20, 2019. Gao, Zilin, Xie, Jiangtao, Wang, Qilong, Li, Peihua, pp. 3024-3033. (Year: 2019).*
(Continued)

Primary Examiner — Chad Dickerson
(74) Attorney, Agent, or Firm — CANTOR COLBURN LLP

(57) ABSTRACT

An infrared image sequence-based sleep quality evaluation system and method. The method comprises: obtaining a plurality of respiratory infrared image sequences to be evaluated, one respiratory infrared image sequence comprising a plurality of respiratory infrared image frames to be
(Continued)

evaluated; performing sleep quality evaluation on each respiratory infrared image sequence in the plurality of respiratory infrared image sequences by means of a classifier to obtain a sleep quality evaluation result corresponding to each respiratory infrared image sequence; and counting the number of different sleep quality evaluation results according to the sleep quality evaluation results respectively corresponding to the plurality of respiratory infrared image sequences, and determining the sleep quality evaluation result with the largest number as a sleep quality evaluation result of a user. Contactless sleep monitoring can be carried out on a user, monitoring costs are reduced at the same time, and evaluation accuracy of sleep quality is improved.

20 Claims, 5 Drawing Sheets

(51) Int. Cl.
*G06T 7/00* (2017.01)
*G06V 10/764* (2022.01)
*G06V 10/774* (2022.01)
*G06V 10/82* (2022.01)

(52) U.S. Cl.
CPC .......... *A61B 5/4815* (2013.01); *A61B 5/7267* (2013.01); *G06V 10/764* (2022.01); *G06V 10/7753* (2022.01); *G06V 10/82* (2022.01); *G06T 2207/10016* (2013.01); *G06T 2207/10048* (2013.01); *G06T 2207/20081* (2013.01); *G06T 2207/20084* (2013.01); *G06T 2207/30196* (2013.01); *G06T 2207/30232* (2013.01)

(58) Field of Classification Search
CPC . G06T 2207/10048; G06T 2207/20081; G06T 2207/20084; G06T 2207/30196; G06T 2207/30232; G06T 7/0012; G06V 10/764; G06V 10/7753; G06V 10/82; G06V 40/20
USPC ......................................................... 382/128
See application file for complete search history.

(56) References Cited

U.S. PATENT DOCUMENTS

| | | | | |
|---|---|---|---|---|
| 2010/0049008 | A1* | 2/2010 | Doherty | A61B 5/4812 128/204.23 |
| 2020/0265219 | A1* | 8/2020 | Liu | G06F 18/214 |
| 2022/0207300 | A1* | 6/2022 | Rho | G06F 18/2148 |
| 2022/0343638 | A1* | 10/2022 | Wang | G16H 30/40 |

FOREIGN PATENT DOCUMENTS

| | | | | |
|---|---|---|---|---|
| CN | 104834946 | A | | 8/2015 |
| CN | 106236013 | A | | 12/2016 |
| CN | 107280673 | A | | 10/2017 |
| CN | 104834946 | B | * | 2/2018 |
| CN | 110647973 | A | * | 1/2020 ............... G06N 3/02 |

OTHER PUBLICATIONS

International Search Report for International Application No. PCT/CN2019/126038; Date of Completion: Aug. 27, 2020; Date of Mailing: Sep. 22, 2020; 4 Pages.

Translation of International Search Report for International Application No. PCT/CN2019/126038; Date of Completion: Aug. 27, 2020; Date of Mailing: Sep. 22, 2020; 2 Pages.

Written Opinion for International Application No. PCT/CN2019/126038; Date of Completion: Sep. 16, 2020; Date of Mailing: Sep. 22, 2020; 3 Pages.

Translation of Written Opinion for International Application No. PCT/CN2019/126038; Date of Completion: Sep. 16, 2020; Date of Mailing: Sep. 22, 2020; 4 Pages.

* cited by examiner

INFRARED IMAGE SEQUENCE-BASED SLEEP QUALITY EVALUATION SYSTEM AND METHOD COMPRISING PERFORMING EVALUATION BY A CLASSIFIER AND COUNTING THE SLEEP QUALITY EVALUATION RESULTS TO DETERMINE THE LARGEST NUMBER TO JUDGE GOOD OR POOR SLEEP QUALITY

CROSS REFERENCE TO RELATED APPLICATION

The present application is a National Stage of PCT Application No. PCT/CN2019/126038 filed on Dec. 17, 2019, the content of which is incorporated herein by reference thereto.

BACKGROUND

Technical Field

The present application involves in the field of deep learning technologies, and in particular relates to a sleep quality evaluation system based on infrared image sequences and a sleep quality evaluation method based on infrared image sequences.

Related Prior Art

Sleep, as a complex life behavior, is closely related to human health, and sleep occupies about one-third of human life. However, pace of modern life is generally accelerating, pressure of life and work is increasing, and sleep loss is becoming more common, thereby seriously affecting quality of people's daily life and even their physical health. Therefore, it is of great significance to detect sleep quality, evaluate people's sleep status, and promptly guide and treat poor sleep.

For the detection of sleep quality, existing methods usually use methods such as multi-channel physiological sleep detection images and capturing physiological data through a wearable device to evaluate the sleep quality of a user. However, the method of multi-channel physiological sleep detection images requires a large number of sensors, and most of the sensors are located on a sensitive head and face, which easily generates physiological discomfort and psychological pressure to a subject and in turn affects the subject's sleep during measurement, thereby causing deviation of a detection result from a real situation; moreover, the multi-channel physiological sleep monitor device is complicated to operate and inconvenient to move, the subject needs to use the relevant equipment to be monitor for about 8 hours in a hospital, which is expensive, and both time cost and price cost of which are relatively high; the method for capturing physiological data, through a wearable device, requires direct contact with a human body when analyzing the sleep quality, which causes inconvenient movement and psychological burden to the subject, results in interference on a sleep process of the subject and affects the subject's sleep habit, thereby ultimately affecting evaluation accuracy of the sleep quality of the subject.

SUMMARY

Embodiments of the present application provide a sleep quality evaluation system based on infrared image sequences and a sleep quality evaluation method based on infrared image sequences, so as to perform contactless sleep monitoring for a user and reduce monitoring cost, thereby improving evaluation accuracy of the sleep quality.

A first aspect of embodiments of the present application provides a sleep quality evaluation method based on infrared image sequences, and the sleep quality evaluation method includes:
  obtaining a plurality of respiratory infrared image sequences to be evaluated, here one respiratory infrared image sequence to be evaluated includes a plurality of respiratory infrared image frames to be evaluated;
  performing sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated;
  counting the number of different sleep quality evaluation results according to the sleep quality evaluation results respectively corresponding to the plurality of respiratory infrared image sequences to be evaluated, and determining one sleep quality evaluation result accounting for the largest number as a sleep quality evaluation result of a user.

A second aspect of embodiments of the present application provides a sleep quality evaluation system based on infrared image sequences, and the sleep quality evaluation system includes:
  an image sequence acquisition module 41 configured to obtain a plurality of respiratory infrared image sequences to be evaluated, here one respiratory infrared image sequence to be evaluated includes a plurality of respiratory infrared image frames to be evaluated;
  a sleep quality evaluation module 42 configured to perform sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated;
  a sleep quality determination module 43 configured to count the number of different sleep quality evaluation results according to the sleep quality evaluation results respectively corresponding to the plurality of respiratory infrared image sequences to be evaluated and determine one sleep quality evaluation result accounting for the largest number as a sleep quality evaluation result of a user.

A third aspect of embodiments of the present application provides a terminal device, which includes a memory, a processor and a computer program stored in the memory and executable on the processor, and the processor, when executing the computer program, implements steps of the sleep quality evaluation method as described above in the first aspect.

A fourth aspect of embodiments of the present application provides a computer-readable storage medium, the computer-readable storage medium stores a computer program, and the computer program, when executed by a processor, implements steps of the sleep quality evaluation method as described above in the first aspect.

A fifth aspect of the present application provides a computer program product, and the computer program product, when executed on a terminal device, causes the terminal device to execute steps of the sleep quality evaluation method as described above in the first aspect.

It can be seen from the above that these solutions use the infrared camera apparatus to obtain the plurality of respiratory infrared image sequences to be evaluated of the user during sleep, which can realize contactless sleep monitoring for the user while reducing the monitoring cost; further, through the classifier based on tensor decomposition, the sleep quality evaluation is performed by taking each respiratory infrared image sequence to be evaluated of the plurality of respiratory infrared image sequences to be evaluated as a whole, which can effectively retain the temporal and spatial continuity information between the respiratory infrared images to be evaluated in each respiratory infrared image sequence to be evaluated, thereby improving the accuracy of the sleep quality evaluation result for each respiratory infrared image sequence to be evaluated; further, the sleep quality evaluation result accounting for the most among the multiple sleep quality evaluation results is used as the user's sleep quality evaluation result, which improves the evaluation accuracy of the user's sleep quality.

BRIEF DESCRIPTION OF THE DRAWINGS

In order to more clearly describe the technical solutions in the embodiments of the present application, drawings needed in the description for the embodiments or the prior art will be briefly introduced below. Obviously, the drawings in the following description are only some embodiments of the present application, and other drawings may be obtained for those of ordinary skill in the art based on these drawings without creative labor.

DETAILED DESCRIPTION

In the following description, for the purpose of illustration rather than limitation, specific details such as a specific system structure and technology etc. are proposed for a thorough understanding of the embodiments of the present application. However, it should be understood to those skilled in the art that the present application can also be implemented in other embodiments without these specific details. In other cases, detailed descriptions of well-known systems, apparatuses, circuits and methods are omitted to avoid unnecessary details from obstructing the description of the present application.

It should be understood that when used in this specification and appended claims, the term "comprising" indicates existence of a described feature, whole, step, operation, element and/or component, but does not exclude existence or addition of one or more other features, wholes, steps, operations, elements, components and/or a combinations thereof.

It should also be understood that the terms used in the specification of the present application are only for the purpose of describing specific embodiments and are not intended to limit the present application. As used in the specification and appended claims of the present application, the singular forms "a", "an" and "the" are intended to include plural forms unless other cases are clearly indicated in the context.

It should be understood that sequence numbers of steps in the embodiments do not mean execution sequences, and the execution sequences of processes should be determined by their functions and internal logic and should not constitute any limitation on implementation processes of the embodiments of the present application.

In order to illustrate the technical solutions described in the present application, specific embodiments are used for description below.

Figure 1:
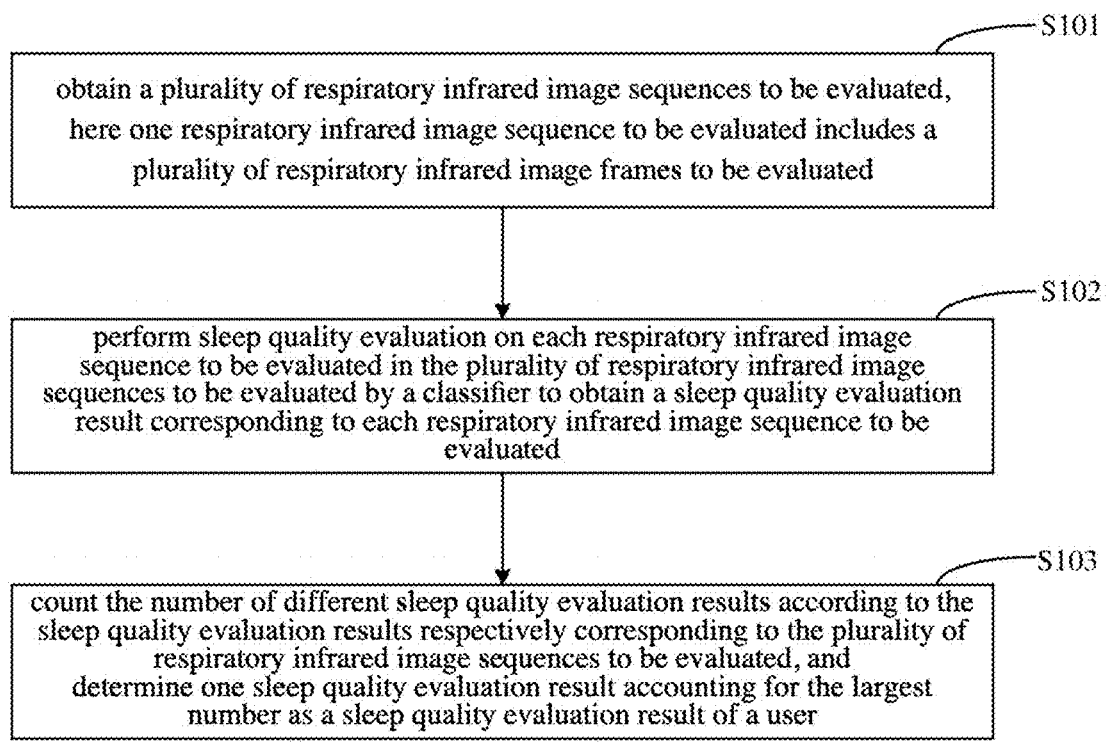
FIG. 1 is a schematic diagram of an implementation process of a sleep quality evaluation method based on infrared image sequences provided by a first embodiment of the present application.

Referring to FIG. 1, FIG. 1 is a schematic diagram of an implementation process of a sleep quality evaluation method based on infrared image sequences provided by a first embodiment of the present application, the sleep quality evaluation method is applied to a terminal device, and the sleep quality evaluation method, as shown in the figure, may include the following steps.

At a step S101, obtain a plurality of respiratory infrared image sequences to be evaluated, here one respiratory infrared image sequence to be evaluated includes a plurality of respiratory infrared image frames to be evaluated.

In an embodiment of the present application, the plurality of respiratory infrared image sequences to be evaluated (that is, at least two respiratory infrared image sequences to be evaluated) of a user during sleep may be acquired through an infrared camera apparatus, and the infrared camera apparatus may be integrated in the terminal device or may be independent of the terminal device (that is, the infrared camera apparatus is not integrated in the terminal device). When the infrared camera apparatus is independent of the terminal device, connection and communication between the infrared camera apparatus and the terminal device be established through a wireless or wired means, to transmit the plurality respiratory infrared image sequences to be evaluated obtained by the camera apparatus to the terminal device. Among them, the respiratory infrared image to be evaluated may refer to an image of a mouth and nose area of the user (that is, the user whose sleep quality is evaluated) taken by the infrared camera apparatus, and the infrared camera apparatus does not require contact with the user and can realize contactless sleep monitoring for the user, thereby avoiding interference to the user's daily sleep while reducing monitoring cost. The continuous acquisition of the plurality of respiratory infrared image frames to be evaluated can capture temperature changes in the mouth and nose area of the user when the user respiratoryes, so as to extract features such as respiratory frequency and respiratory depth. One respiratory infrared image sequence to be evaluated may refer to one respiratory infrared image sequence waiting to be evaluated for sleep quality.

When the infrared camera apparatus acquires the plurality of respiratory infrared image sequences to be evaluated while the user is sleeping, the respiratory infrared image sequence to be evaluated while the user is sleeping may be collected by using a sliding window with a preset duration as a basic unit, for example, one minute is used as one basic unit, the respiratory infrared images to be evaluated are continuously collected for five minutes, the plurality of respiratory infrared image frames to be evaluated within one minute form one respiratory infrared image sequence to be evaluated, and five minutes include five minutes, that is, five minutes correspond to five respiratory infrared image sequences to be evaluated.

Optionally, before each respiratory infrared image sequence to be evaluated is input into a classifier, preprocessing may also be performed on each respiratory infrared image sequence to be evaluated, and the preprocessing includes, but is not limited to, adjusting sizes of the plurality of respiratory infrared image frames to be evaluated in each respiratory infrared image sequence to be evaluated to be the same (for example, adjusting them to a preset size) and/or adjusting pixel values of the plurality of respiratory infrared image frames to be evaluated in each respiratory infrared image sequence to be evaluated to be within a preset range.

At a step S102, perform sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated.

Among them, the above-mentioned classifier can evaluate the respiratory infrared image sequence to be evaluated as a whole for sleep quality evaluation, that is, the above-mentioned classifier can directly evaluate one respiratory infrared image sequence to be evaluated for sleep quality, which can effectively retain temporal and spatial continuity information between the plurality of respiratory infrared image frames to be evaluated in one respiratory infrared image sequence to be evaluated, and improves the accuracy of the sleep quality evaluation result of one respiratory infrared image sequence to be evaluated. The sleep quality evaluation result is used to indicate whether the sleep quality is good or poor, and the sleep quality evaluation result includes, but is not limited to, a first sleep quality evaluation result and a second sleep quality evaluation result, the first sleep quality evaluation result may refer to a good sleep quality, and the second sleep quality evaluation result may refer to a poor sleep quality, that is, the sleep quality indicated by the first sleep quality evaluation result is better than the sleep quality indicated by the second sleep quality evaluation result. It should be noted that the content of the sleep quality evaluation result may further be divided again according to actual needs, for example, the sleep quality evaluation result may includes excellent sleep quality, good sleep quality, poor sleep quality, etc., which is not limited here. It should be noted that performing sleep quality evaluation on one respiratory infrared image sequence to be evaluated by the classifier is to classify one respiratory infrared image sequence to be evaluated, and classification categories correspond to the sleep quality evaluation results, for example, the classification categories include good sleep quality and poor sleep quality, and whether the category of one respiratory infrared image sequence to be evaluated indicates good sleep quality or poor sleep quality is determined by the classifier.

It should be noted that, when the sleep quality evaluation is performed on each respiratory infrared image sequence to be evaluated in the plurality of respiratory infrared image sequences to be evaluated by the classifier, the classifier may perform the sleep quality evaluation on the plurality of respiratory infrared image sequences to be evaluated respectively after the plurality of respiratory infrared image sequences to be evaluated are obtained; alternatively, the classifier may perform the sleep quality evaluation on a first respiratory infrared image sequence to be evaluated after the first respiratory infrared image sequence to be evaluated is obtained, so as to obtain a sleep quality evaluation result of the first respiratory infrared image sequence to be evaluated (i.e., the sleep quality evaluation result corresponding to the first respiratory infrared image sequence to be evaluated), and the classifier may perform the sleep quality evaluation on a second respiratory infrared image sequence to be evaluated after the second respiratory infrared image sequence to be evaluated is obtained, so as to obtain a sleep quality evaluation result of the second respiratory infrared image sequence to be evaluated, and the rest can be done in the same manner until a sleep quality evaluation result of the last one respiratory infrared image sequence to be evaluated in the plurality of respiratory infrared image sequences to be evaluated is obtained. For example, when the infrared camera apparatus collects the respiratory infrared image sequence to be evaluated minute by minute (that is, one minute is used as one basic unit), the sleep quality evaluation may be performed minute by minute, and statistics is performed on the sleep quality evaluation results of the respiratory infrared image sequences to be evaluated every minute.

Optionally, the performing sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated includes:

inputting each of the respiratory infrared image sequences to be evaluated into the classifier;

acquiring a target feature image of each of the respiratory infrared image sequences to be evaluated according to a second-order pooling block and a tensor decomposition-based network layer in the classifier;

performing sleep quality evaluation on each of the respiratory infrared image sequences to be evaluated according to the target feature image and a tensor decomposition-based full connection layer in the classifier to obtain the sleep quality evaluation result corresponding to each of the respiratory infrared image sequences to be evaluated.

In an embodiment of the present application, when the classifier receives one respiratory infrared image sequence to be evaluated, sleep-related respiratory features may be extracted automatically through using second-order information of the respiratory infrared image sequence to be evaluated by the second-order pooling block under a self-attentional mechanism, thereby improving the evaluation accuracy of the sleep quality of the respiratory infrared image sequence to be assessed. The tensor decomposition-based network layer includes a tensor decomposition-based convolutional layer and two tensor decomposition-based dense connection blocks, and the classifier uses a dense connection mechanism of the dense connection blocks to effectively solve a problem of gradient disappearance. Among them, the dense connection block in the classifier may refer to a dense convolutional neural network, such as a residual network. One dense connection block usually includes a plurality of convolutional layers. The tensor decomposition-based convolutional layer refers to tensor decomposition of a convolution kernel of a convolutional layer, the tensor decomposition-based convolutional layer is a 3D convolutional layer, and the tensor decomposition of the convolution kernel of the 3D convolutional layer may decompose the convolution kernel of the 3D convolutional layer into product of two matrices and one three-dimensional tensor, here first and third orders are matrices, and a second order is a three-dimensional tensor.

The tensor decomposition-based full connection layer refers to tensor decomposition of weights of a full connection layer, which may decompose the weights of the full connection layer into product of two matrices and one three-dimensional tensor, here first and third orders are matrices, and a second order is a three-dimensional tensor.

In an embodiment of the present application, after one respiratory infrared image sequence to be evaluated is input into the classifier, the respiratory infrared image sequence to be evaluated is first taken as a tensorized whole, which is to be convolved with the tensor-decomposed convolution kernel in the convolutional layer, a result of which is then to be convolved with the tensor-decomposed convolution kernel in one dense connection block, a result of which is then to be convolved with tensor-decomposed convolution sum in one dense connection block after passing through the second-order pooling block, and finally the sleep quality evaluation result of the respiratory infrared image sequence to be evaluated is obtained by weighting the tensor-decomposed full connection layer. The target feature image is a feature image output by the last one dense connection block in the classifier, which is a high-order feature image generated after multi-layer convolution, and which is named as high-order feature image because the last one dense connection block in the classifier outputs a plurality of feature images. Among them, the network layer and the full connection layer in the classifier are represented via tensor decomposition, which can reduce the number of parameters in the classifier, and solve problems of loss of internal structure information of tensor data due to vectorization calculation of tensorized data and storage space consumption due to excessive parameters in the classifier. The aforementioned tensor decomposition may refer to Tensor-Train tensor decomposition.

At a Step S103, count the number of different sleep quality evaluation results according to the sleep quality evaluation results respectively corresponding to the plurality of respiratory infrared image sequences to be evaluated, and determine one sleep quality evaluation result accounting for the largest number as a sleep quality evaluation result of a user.

Among them, one respiratory infrared image sequence to be evaluated corresponds to one sleep quality evaluation result, then the plurality of respiratory infrared image sequences to be evaluated correspond to the plurality of sleep quality evaluation results, and the plurality of sleep quality evaluation results may possibly contain the same sleep quality evaluation result therein.

Exemplarily, the classifier respectively process five respiratory infrared image sequences to be evaluated, the sleep quality evaluation results of the first respiratory infrared image sequence to be evaluated, the second respiratory infrared image sequence to be evaluated and the fifth respiratory infrared image sequence to be evaluated indicate good sleep quality, the sleep quality evaluation results of the third respiratory infrared image sequence to be evaluated and the fourth respiratory infrared image sequence to be evaluated indicate poor sleep quality, it is counted that there are three good sleep quality and two poor sleep quality in the five sleep quality evaluation results, and the number of good sleep quality is the largest, then it can be determined that the user's sleep quality evaluation result indicates good sleep quality.

In the embodiments of the present application, the user's respiratory infrared image sequences to be evaluated while sleeping are acquired by the infrared camera apparatus, and the sleep quality evaluation is performed, by the tensor decomposition-based classifier, on each respiratory infrared image sequence to be evaluated which is taken as a whole, such that the contactless sleep quality evaluation can be achieved, thereby improving the evaluation accuracy for the user's sleep quality.

Figure 2:
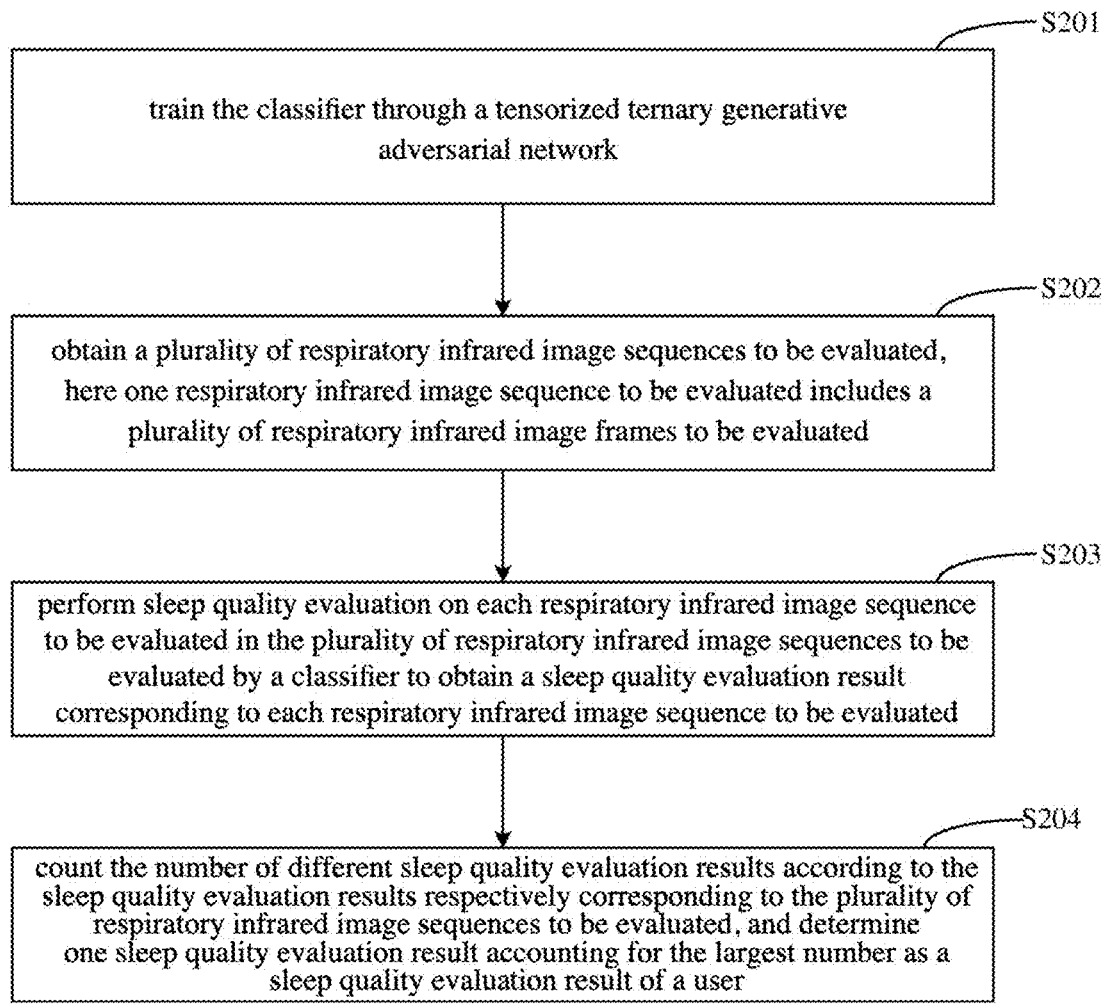
FIG. 2 is a schematic diagram of an implementation process of a sleep quality evaluation method based on infrared image sequences provided by a second embodiment of the present application.

Refer to FIG. 2, which is a schematic diagram of an implementation process of the sleep quality evaluation method based on infrared image sequences provided by a second embodiment of the present application. The sleep quality evaluation method is applied to a terminal device, and the sleep quality evaluation method, as shown in the figure, may include the following steps.

At a step S201, train the classifier through a tensorized ternary generative adversarial network.

Figure 3A:
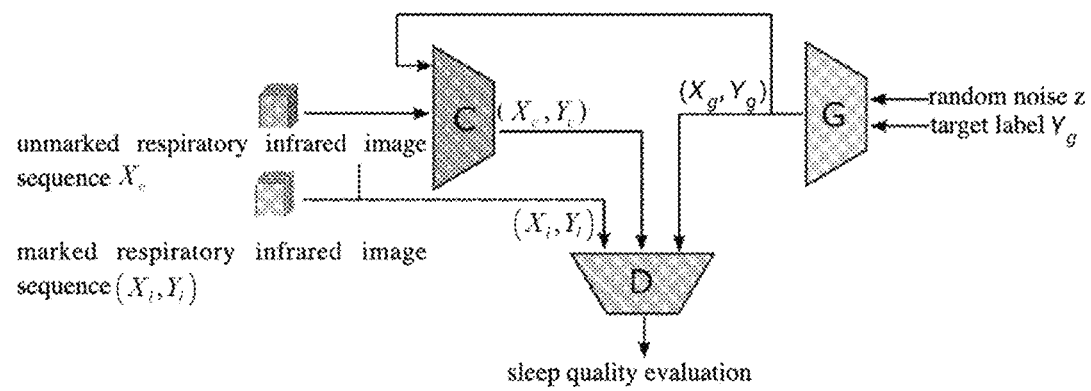
FIG. 3A is an exemplary structural diagram of a tensorized ternary generative adversarial network.

Among them, the tensorized ternary generative adversarial network includes a generator, a classifier, and a discriminator, and the generator, the classifier and the discriminator all adopt tensor decomposition, which effectively reduces the number of parameters in the generator, the classifier and the discriminator, and can realize overall processing of the respiratory infrared image sequence. As shown in FIG. 3A, FIG. 3A is a structural example diagram of the tensorized ternary generative adversarial network, where G represents the generator, C represents the classifier, and D represents the discriminator, the unmarked respiratory infrared image sequence $X_c$, is respiratory infrared image sequence carrying no label, the marked infrared image sequence $(X_l, Y_l)$ is a respiratory infrared image sequence carrying a label, $Y_c$ is the label of the unmarked infrared image sequence, and $X_g$ is a respiratory infrared image sequence generated by the generator.

The tensor decomposition algorithm Tensor-Train decomposes a d-order tensor into product of two matrices and d-2 three-dimensional tensors, where the first and d-th are matrices, the remaining include d-2 three-dimensional tensors, and d is an integer greater than 2. For example, the d-order tensor A may be expressed as $A(l_1, l_2, \ldots, l_d) = G(l_1)G(l_2) \ldots G(l_d)$ after decomposition, where $G(l_1)$ and $G(l_d)$ are matrices, and $G(l_2)$ is a three-dimensional tensor.

Optionally, the training the classifier through a tensorized ternary generative adversarial network includes:
inputting one-dimensional random noise and a target label into the generator, and obtaining a first respiratory infrared image sequence carrying the target label through a tensor decomposition-based deconvolutional layer in the generator;
inputting the first respiratory infrared image sequence into the discriminator, and obtaining a discrimination result of the first respiratory infrared image sequence by the discriminator through a tensor decomposition-based network layer and full connection layer in the discriminator;
training the generator according to the discrimination result;
acquiring a second respiratory infrared image sequence carrying no label;
inputting the second respiratory infrared image sequence into the classifier, and acquiring a third respiratory infrared image sequence through a second-order pooling block and a tensor decomposition-based network layer and full connection layer in the classifier, here the third respiratory infrared image sequence refers to a second respiratory infrared image sequence carrying a label;

acquiring a fourth respiratory infrared image sequence carrying a label;

training the discriminator according to the first respiratory infrared image sequence, the third respiratory infrared image sequence and the fourth respiratory infrared image sequence, and acquiring a discrimination result of the third respiratory infrared image sequence by the discriminator;

training the classifier according to the first respiratory infrared image sequence, the discrimination result of the third respiratory infrared image sequence by the discriminator and the fourth respiratory infrared image sequence.

Figure 3B:
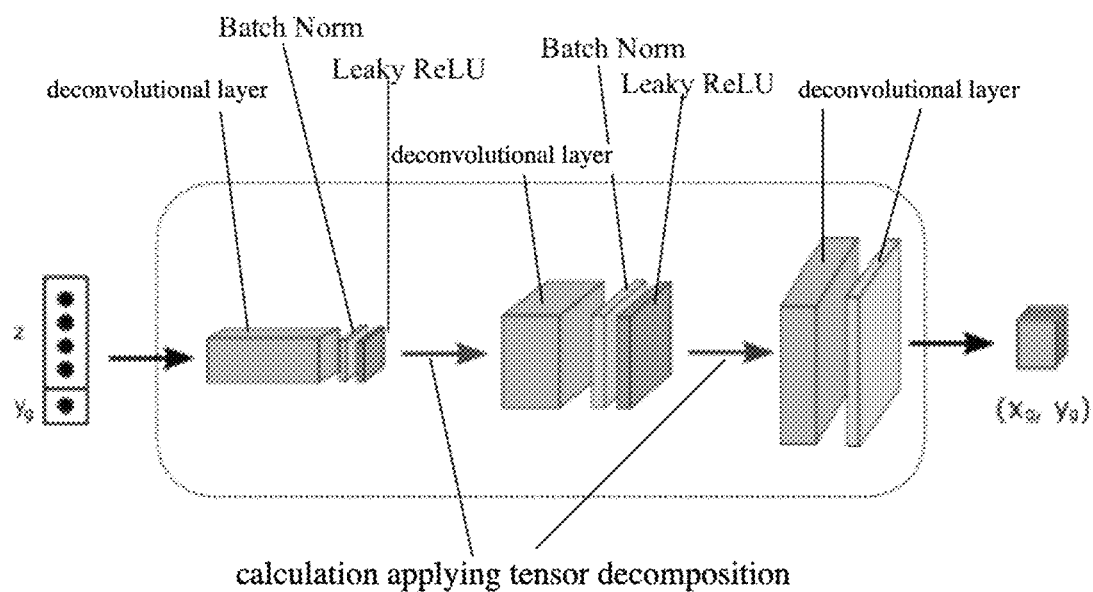
FIG. 3B is an exemplary structural diagram of a generator.

In an embodiment of the present application, the generator adopts the idea of conditional generative adversarial network, one-dimensional random noise that is consistent with a normal distribution is taken as the input of the generator, and sleep quality, as the target label, is taken as a condition for input. The intermediate network layer uses a 3D deconvolutional layer, and then uses Leaky ReLU as an activation function, and uses Batch Norm for batch regularization. The last 3D deconvolutional layer of the generator is followed by one tanh activation layer, and the Tensor-Train tensor decomposition assists the generator to generate the respiratory infrared image sequence carrying the sleep quality label, thereby reducing the need for real respiratory infrared image sequences carrying the labels. FIG. 3B shows an exemplary structural diagram of the generator. Among them, the one-dimensional random noise carrying the target label sequentially passes through the 3D deconvolutional layer, the Leaky ReLU activation function and the batch regularization to perform the gradual deconvolution of the feature image, such that the first respiratory infrared image sequence carrying the target label and approaching reality can be generated.

The first respiratory infrared image sequence generated by the generator is input into the discriminator to obtain the discrimination result of the first respiratory infrared image sequence by the discriminator, a loss function of the generator is obtained according to the discrimination result, and the generator is trained according to the loss function. The loss function of the generator may be expressed as $Loss_G = \log(1-D(x_g, y_g)) + \lambda \|x_{label} - x_g\|_{L_1}$, where $D(x_g, y_g)$ represents the discrimination result of the discriminator, $D(x_g, y_g)$ is equal to 1 if the discrimination result is true, and $D(x_g, y_g)$ is equal to 0 if the discrimination result is false; $\lambda$ is a weight parameter (which may be set by the user according to actual needs); $x_{label}$ is a real respiratory infrared image sequence, $x_g$ is a generated respiratory infrared image sequence (i.e. the first respiratory infrared image sequence), $\|x_{label} - x_g\|_{L_1}$ represents $L_1$ loss of the real respiratory infrared image sequence and the generated respiratory infrared image sequence, such that the generated respiratory infrared image sequence approaches the real respiratory infrared image sequence.

The respiratory infrared image sequences collected by the infrared camera apparatus and carrying no label are divided into two parts: one part is used as the second respiratory infrared image sequence on which the sleep quality evaluation is performed by the classifier, and the sleep quality evaluation result output by the classifier is used as the label, so as to obtain the third respiratory infrared image sequence; the other part needs a sleep expert to evaluate the sleep quality, and the sleep quality evaluation result is used as the label, so as to obtain the fourth respiratory infrared image sequence carrying a label; the first respiratory infrared image sequence, the third respiratory infrared image sequence and the fourth respiratory infrared image sequence are respectively input to the discriminator to obtain the discrimination results of the first, third and fourth respiratory infrared image sequences by the discriminator. A loss function of the discriminator is obtained according to the discriminant results of the above three respiratory infrared image sequences, and the discriminator is trained according to this loss function. The loss function of the discriminator may be expressed as $Loss_D = \log D(x_l, y_l) + \alpha \log(1 - D(x_c, y_c)) + (1-\alpha)\log(1 - D(x_g, y_g))$, where $D(x_l, y_l)$ is the discrimination result of the fourth respiratory infrared image sequence, $D(x_c, y_c)$ is the discrimination result of the third respiratory infrared image sequence, $D(x_g, y_g)$ is the discrimination result of the first respiratory infrared image sequence, $\alpha$ is a weight parameter (which may be set by the user according to actual needs, and $\alpha$ is greater than or equal to 0, and less than or equal to 1).

The first respiratory infrared image sequence and the fourth respiratory infrared image sequence are input into the classifier respectively to perform classification training on the classifier, and a loss function $Loss_g$ is obtained when the first respiratory infrared image sequence is used to train the classifier and a loss function $Loss_l$ is obtained when the fourth respiratory infrared image sequence is used to train the classifier, and $Loss_g$ and $Loss_l$ are integrated as $Loss_{supervised} = Loss_g + \alpha Loss_l$. According to the discrimination result of the third respiratory infrared image sequence by the discriminator, a loss function $Loss_{unsupervised}$ is obtained when the classifier performs classification on the second respiratory infrared image sequence, and a loss function of the classifier may be expressed as $Loss_c = Loss_{supervised} + Loss_{unsupervised}$.

In an embodiment of the present application, the tensorized ternary generative adversarial network uses a large number of second respiratory infrared image sequences (i.e., respiratory infrared image sequences carrying no label) and a small number of fourth respiratory infrared image sequences (i.e. respiratory infrared image sequences carrying a label) to train the tensorized ternary generative adversarial network, which can solve the problem of less respiratory infrared image sequence data carrying a label and at the same time make full use of the respiratory infrared image sequences carrying no label, thereby facilitating improvement of the robustness of the tensorized ternary generative adversarial network.

Optionally, the obtaining a first respiratory infrared image sequence carrying the target label through a tensor decomposition-based deconvolutional layer in the generator includes:

performing tensor decomposition on a deconvolution kernel of the deconvolutional layer in the generator to obtain a first tensor;

performing deconvolution calculation on the one-dimensional random noise and the first tensor to obtain the first respiratory infrared image sequence carrying the target label.

In an embodiment of the present application, after the deconvolution kernel of the 3D deconvolutional layer in the generator is tensor-decomposed, it can be decomposed into product of two matrices and one three-dimensional tensor (where the first order and the third order are matrices, the second order is the three-dimensional tensor), and then the input one-dimensional random noise and the first tensor (that is, the product of two matrices and one three-dimensional tensor) are subjected to multi-layer deconvolution calculations, and then the first respiratory infrared image sequence carrying the target label and approaching reality is generated through an activation function Leaky ReLU, batch regularization and a tanh activation layer in the exemplary structural diagram as shown in FIG. 3B.

Optionally, the tensor decomposition-based network layer in the discriminator includes a tensor decomposition-based convolutional layer, a first dense connection block and a second dense connection block; and the obtaining a discrimination result of the first respiratory infrared image sequence by the discriminator through a tensor decomposition-based network layer and full connection layer in the discriminator includes:

performing tensor decomposition on a convolution kernel of the convolutional layer in the discriminator to obtain a second tensor;

convolving the first respiratory infrared image sequence with the second tensor to obtain a first feature image;

performing tensor decomposition on a convolution kernel of the first dense connection block in the discriminator to obtain a third tensor;

convolving the first feature image with the third tensor to obtain a second feature image;

performing tensor decomposition on a convolution kernel of the second dense connection block in the discriminator to obtain a fourth tensor;

convolving the second feature image with the fourth tensor to obtain a third feature image;

performing tensor decomposition on weights of the full connection layer in the discriminator to obtain a fifth tensor;

obtaining the discrimination result of the first respiratory infrared image sequence by the discriminator according to the third feature image and the fifth tensor;

among them, the first feature image, the second feature image and the third feature image are all feature images of the first respiratory infrared image sequence.

In the embodiments of the present application, after tensor decomposition is performed on the convolution kernel of the 3D convolutional layer in the discriminator, it may be decomposed into the product of two matrices and one three-dimensional tensor (where the first order and the third order are matrices, and the second order is one three-dimensional tensor), the product of the decomposed two matrices and one three-dimensional tensor constitutes the second tensor, and the feature image obtained by performing multiple layers of convolution calculations on the first respiratory infrared image sequence through the second tensor constitutes the first feature image; after tensor decomposition is performed on the convolution kernel of the first dense connection block in the discriminator, it may be decomposed into the product of two matrices and one three-dimensional tensor (where the first order and the third order are matrices, and the second order is one three-dimensional tensor), the product of the decomposed two matrices and one three-dimensional tensor constitutes the third tensor, and the feature image obtained by performing multiple layers of convolution calculations on the first feature image through the third tensor constitutes the second feature image; after tensor decomposition is performed on the convolution kernel of the second dense connection block in the discriminator, it may be decomposed into the product of two matrices and one three-dimensional tensor (where the first and third orders are matrices, and the second order is one three-dimensional tensor), the product of the decomposed two matrices and one three-dimensional tensor constitutes the fourth tensor, and the feature image obtained by performing multiple layers of convolution calculations on the second feature image through the fourth tensor constitutes the third feature image; tensor decomposition is performed on the weights of the full connection layer in the discriminator, and it may be decomposed into the product of two matrices and one three-dimensional tensor (where the first order and the third order are matrices, and the second order is one three-dimensional tensor), the product of the decomposed two matrices and one three-dimensional tensor constitutes the fifth tensor, and the third feature image can achieve discrimination of true and false of the first respiratory infrared image sequence through the fifth tensor.

Optionally, the discriminator further includes a first transition layer and a second transition layer, the first transition layer and the second transition layer are both 1×1×1 convolution kernels; the first transition layer is located between the first dense connection block and the second dense connection block in the discriminator to reduce the number of the second feature images; the second transition layer is located between the second dense connection block and the full connection block in the discriminator to reduce the number of the third feature images.

In the embodiments of the present application, after the first feature image is convolved with the first dense connection block, the number of the obtained second feature images increases, and the number of the second feature images can be reduced through performing convolution calculation through the 1×1×1 3D convolution kernel, i.e., the number of channels is reduced. After the second feature images are convolved with the second dense connection block, the number of the obtained third feature images increases, and the number of the third feature images can be reduced through performing convolution calculation through the 1×1×1 3D convolution kernel, i.e., the number of channels is reduced.

Figure 3C:
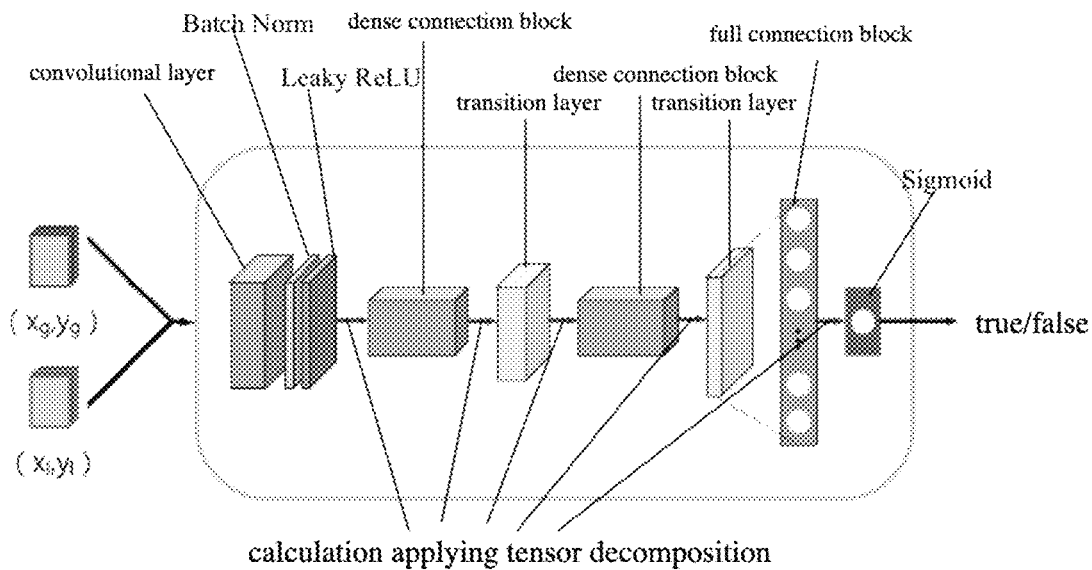
FIG. 3C is an exemplary structural diagram of a discriminator.

FIG. 3C shows an exemplary structural diagram of the discriminator, the respiratory infrared image sequence carrying a label and input into the discriminator (may be any respiratory infrared image sequence carrying a label and input into the discriminator) passes through the deep neural network including the tensor decomposition-based convolutional layer (i.e. 3D tensorized convolutional layer), the tensor decomposition-based dense connection block (i.e. 3D tensorized dense connection block), the transition layer and the tensor decomposition-based full connection layer, so as to extract features from the respiratory infrared image sequence, such that the spatial and temporal respiratory feature information of the respiratory infrared image sequence is retained. The extracted respiratory feature information is finally input into one tensor decomposition-based full connection layer to realize discrimination of true and false of the respiratory infrared image sequence carrying a label. The discriminator further includes a Leaky ReLU activation function, Batch Norm regularization and a sigmoid function.

For the discriminator, the embodiments of the present application use the dense connection block to directly input the feature images extracted by the network layer located before the dense connection block into the subsequent network layer for cascading, to reduce feature loss during the gradient transfer process, solve a problem of gradient disappearance during a back propagation process of the deep neural network and stabilize the training of the adversarial generative network, thereby improving the discrimination performance of the discriminator on generated samples and real samples.

Optionally, the tensor decomposition-based network layer in the classifier includes a tensor decomposition-based convolutional layer, a third dense connection block and a fourth dense connection block; and the acquiring a third respiratory infrared image sequence through a second-order pooling block and a tensor decomposition-based network layer and full connection layer in the classifier includes:

performing tensor decomposition on a convolution kernel of the convolutional layer of the classifier to obtain a sixth tensor;

convolving the second respiratory infrared image sequence with the sixth tensor to obtain a fourth feature image;

performing tensor decomposition on a convolution kernel of the third dense connection block of the classifier to obtain a seventh tensor;

convolving the fourth feature image with the seventh tensor to obtain a fifth feature image;

processing the fifth feature image by using the second-order pooling block of the classifier to obtain a sixth feature image;

performing tensor decomposition on a convolution kernel of the fourth dense connection block of the classifier to obtain an eighth tensor;

convolving the sixth feature image with the eighth tensor to obtain a seventh feature image;

performing tensor decomposition on weights of the full connection block of the classifier to obtain a ninth tensor;

obtaining the third respiratory infrared image sequence according to the seventh feature image and the ninth tensor;

among them, the fourth feature image, the fifth feature image, the sixth feature image and the seventh feature image are all feature images of the second respiratory infrared image sequence.

In the embodiments of the present application, after tensor decomposition of the convolution kernel of the 3D convolutional layer in the classifier, it may be decomposed into the product of two matrices and one three-dimensional tensor (where the first order and the third order are matrices, and the second order is one three-dimensional tensor), the product of the decomposed two matrices and one three-dimensional tensor constitutes the sixth tensor, and the feature image obtained by performing multiple layers of convolution calculations on the second respiratory infrared image sequence through the sixth tensor constitutes the fourth feature image; after tensor decomposition of the convolution kernel of the third dense connection block in the classifier, it may be decomposed into the product of two matrices and one three-dimensional tensor (where the first order and the third order are matrices, and the second order is one three-dimensional tensor), the product of the decomposed two matrices and one three-dimensional tensor constitutes the seventh tensor, and the feature image obtained by performing multiple layers of convolution calculations on the fourth feature image through the seventh tensor constitutes the fifth feature image; the feature image obtained after the fifth feature image is processed by the second-order pooling block constitutes the sixth feature image; after tensor decomposition of the convolution kernel of the fourth dense connection block in the classifier, it may be decomposed into the product of two matrices and one three-dimensional tensor (where the first and third orders are matrices, and the second order is one three-dimensional tensor), and the product of the decomposed two matrices and one three-dimensional tensor constitutes the eighth tensor, and the feature image obtained by performing multiple layers of convolution calculations on the sixth feature image through the eighth tensor constitutes the seventh feature image; tensor decomposition is performed on the weights of the full connection block in the classifier so as to decompose it into the product of two matrices and one three-dimensional tensor (where the first and third orders are matrices, and the second order is one three-dimensional tensor), the product of the decomposed two matrices and one three-dimensional tensor constitutes the ninth tensor, and the seventh feature image can obtain a probability value of a corresponding category through the ninth tensor, so as to obtain the sleep quality evaluation result of the second respiratory infrared image sequence (that is, the label of the second respiratory infrared image).

Optionally, the classifier further includes a third transition layer and a fourth transition layer, and the third transition layer and the fourth transition layer are both 1×1×1 convolution kernels; the third transition layer is located between the second-order pooling block and the fourth dense connection block in the classifier to reduce the number of the sixth feature images; and the fourth transition layer is located between the fourth dense connection block and the full connection layer in the classifier to reduce the number of the seventh feature images.

In the embodiments of the present application, after the fourth feature image is convolved through the third dense connection block, the number of the obtained fifth feature images increases, which in turn leads to a larger number of sixth feature images processed by the second-level pooling block, the number of the sixth feature images may be reduced through the convolution calculation by the 1×1×1 3D convolution kernel, that is, the number of channels can be reduced. After the sixth feature images are convolved by the fourth dense connection block, the number of the obtained seventh feature images increases, and the number of the seventh feature images can be reduced through convolution calculation by the 1×1×1 3D convolution kernel, that is, the number of channels is reduced.

Figure 3D:
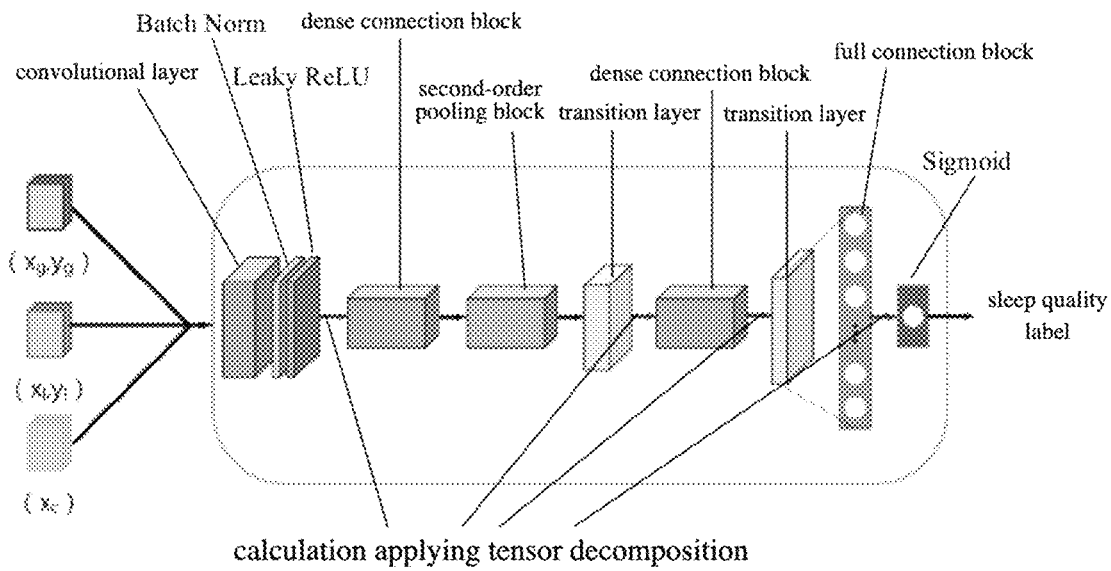
FIG. 3D is an exemplary structural diagram of a classifier.

FIG. 3D shows an exemplary structural diagram of the classifier. The multiple layers of convolution calculations are performed on the respiratory infrared image sequence input to the classifier through a tensor decomposition-based convolutional layer (i.e. 3D tensorized convolutional layer) and a tensor decomposition-based dense connection block (i.e. 3D tensorized dense connection block), and the number of the feature images is reduced through the transition layers, and then the probability value of the corresponding category may be obtained through a tensor decomposition-based full connection layer, thereby obtaining the sleep quality evaluation result of the respiratory infrared image sequence. The classifier further includes a Leaky ReLU activation function, Batch Norm regularization and a sigmoid function.

For the classifier, the embodiments of the application use a self-attention mechanism of the dense connection block based on second-order pooling to weight the feature images in a dimension of the feature channels according to the correlation of different regions, so that the weight of the important channel is significant, and the weight of unimportant channel is small, which can effectively extract the respiratory features in the infrared image sequence and improve the evaluation accuracy for sleep quality.

At a step S202, obtain a plurality of respiratory infrared image sequences to be evaluated, here one respiratory infrared image sequence to be evaluated includes a plurality of respiratory infrared image frames to be evaluated.

This step is the same as the step S101. For details, please refer to the related description of the step S101, which will not be repeated herein again.

At a step S203, perform sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated.

This step is the same as the step S102. For details, please refer to the related description of the step S102, which will not be repeated herein again.

At a step S204, count the number of different sleep quality evaluation results according to the sleep quality evaluation results respectively corresponding to the plurality of respiratory infrared image sequences to be evaluated, and determine one sleep quality evaluation result accounting for the largest number as a sleep quality evaluation result of a user.

This step is the same as the step S103. For details, please refer to the related description of step S103, which will not be repeated herein again.

In the embodiments of the present application, the entire ternary generative adversarial network is tensorized, so that this network is provided with a regularization effect, thereby reducing the possibility of network overfitting and enhancing the prediction and generalization capabilities of this network. At the same time, the tensorization reduces network parameters, accelerates the training speed of this network, and increases the network operation efficiency. Additionally, in the embodiments of the present application, through tensorization of the respiratory infrared image sequence and replacement of the 2D convolution with the 3D convolution, the time sequence feature information is effectively extracted, while the noise and unnecessary redundant information are removed and the feature relationship between the respiratory infrared image sequences is retained, thereby reducing the loss of time sequence feature information and improving the classification capability and classification accuracy of the classifier.

Figure 4:
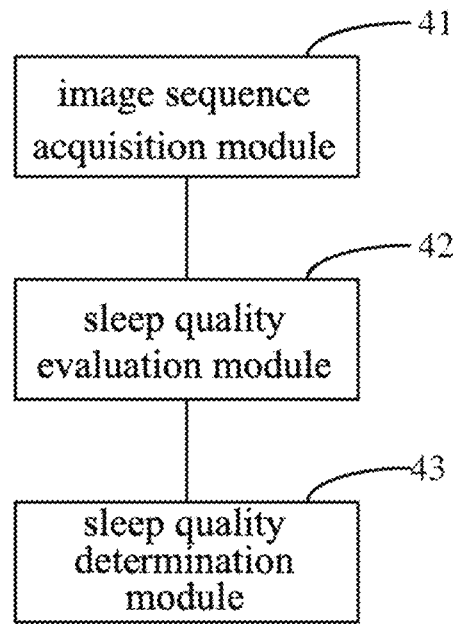
FIG. 4 is a schematic structural diagram of a sleep quality evaluation system based on infrared image sequences provided by a third embodiment of the present application.

Referring to FIG. 4, FIG. 4 is a schematic diagram of a sleep quality evaluation system based on infrared image sequences provided by a third embodiment of the present application. For ease of description, only the parts related to the embodiments of the present application are shown.

The sleep quality evaluation system includes:
- an image sequence acquisition module 41 configured to obtain a plurality of respiratory infrared image sequences to be evaluated, here one respiratory infrared image sequence to be evaluated includes a plurality of respiratory infrared image frames to be evaluated;
- a sleep quality evaluation module 42 configured to perform sleep quality evaluation on each respiratory infrared image sequence to be evaluated in the plurality of respiratory infrared image sequences to be evaluated by a classifier to obtain a sleep quality evaluation result corresponding to each respiratory infrared image sequence to be evaluated;
- a sleep quality determination module 43 configured to count the number of different sleep quality evaluation results according to the sleep quality evaluation results respectively corresponding to the plurality of respiratory infrared image sequences to be evaluated and determine one sleep quality evaluation result accounting for the largest number as a sleep quality evaluation result of a user.

Optionally, the sleep quality evaluation module 42 includes:
- a sequence inputting unit configured to input each of the respiratory infrared image sequences to be evaluated into the classifier;
- a target feature image acquisition unit configured to acquire a target feature image of each of the respiratory infrared image sequences to be evaluated according to a second-order pooling block and a tensor decomposition-based network layer of the classifier;
- an evaluation result acquisition unit configured to perform sleep quality evaluation on each of the respiratory infrared image sequences to be evaluated according to the target feature image and a tensor decomposition-based full connection layer of the classifier to obtain the sleep quality evaluation result corresponding to each of the respiratory infrared image sequences to be evaluated.

Optionally, the sleep quality evaluation system further includes:
- a classifier training module configured to train the classifier through a tensorized ternary generative adversarial network.

Optionally, the tensorized ternary generative adversarial network includes a generator, the classifier and a discriminator; and the classifier training module includes:
- a first processing unit configured to: input one-dimensional random noise and a target label into the generator, and obtain a first respiratory infrared image sequence carrying the target label through a tensor decomposition-based deconvolutional layer of the generator;
- a second processing unit configured to: input the first respiratory infrared image sequence into the discriminator, and obtain a discrimination result of the first respiratory infrared image sequence by the discriminator through a tensor decomposition-based network layer and a full connection layer of the discriminator;
- a first training unit configured to train the generator according to the discrimination result;
- a first acquisition unit configured to acquire a second respiratory infrared image sequence carrying no label;
- a third processing unit configured to: input the second respiratory infrared image sequence into the classifier, and acquire a third respiratory infrared image sequence through the second-order pooling block, the tensor decomposition-based network layer and the full connection layer of the classifier, here the third respiratory infrared image sequence refers to a second respiratory infrared image sequence carrying a label;
- a second acquisition unit configured to acquire a fourth respiratory infrared image sequence carrying a label;
- a second training unit configured to: train the discriminator according to the first respiratory infrared image sequence, the third respiratory infrared image sequence and the fourth respiratory infrared image sequence, and acquire a discrimination result of the third respiratory infrared image sequence by the discriminator;
- a third training unit configured to train the classifier according to the first respiratory infrared image sequence, the discrimination result of the third respiratory infrared image sequence by the discriminator and the fourth respiratory infrared image sequence.

Optionally, the first processing unit is specifically configured to:
- perform tensor decomposition on a deconvolution kernel of the deconvolutional layer of the generator to obtain a first tensor;
- perform deconvolution calculation on the one-dimensional random noise and the first tensor to obtain the first respiratory infrared image sequence carrying the target label.

Optionally, the tensor decomposition-based network layer of the discriminator includes a tensor decomposition-based convolutional layer, a first dense connection block and a second dense connection block; and the second processing unit is specifically configured to:

perform tensor decomposition on a convolution kernel of the convolutional layer of the discriminator to obtain a second tensor;

convolve the first respiratory infrared image sequence with the second tensor to obtain a first feature image;

perform tensor decomposition on a convolution kernel of the first dense connection block of the discriminator to obtain a third tensor;

convolve the first feature image with the third tensor to obtain a second feature image;

perform tensor decomposition on a convolution kernel of the second dense connection block of the discriminator to obtain a fourth tensor;

convolve the second feature image with the fourth tensor to obtain a third feature image;

perform tensor decomposition on weights of the full connection layer of the discriminator to obtain a fifth tensor;

obtain the discrimination result of the first respiratory infrared image sequence by the discriminator according to the third feature image and the fifth tensor;

among them, the first feature image, the second feature image and the third feature image are all feature images of the first respiratory infrared image sequence.

Optionally, the discriminator further includes a first transition layer and a second transition layer, the first transition layer and the second transition layer are both 1×1×1 convolution kernels; the first transition layer is located between the first dense connection block and the second dense connection block of the discriminator to reduce the number of the second feature image; the second transition layer is located between the second dense connection block and the full connection block of the discriminator to reduce the number of the third feature image.

Optionally, the tensor decomposition-based network layer of the classifier includes a tensor decomposition-based convolutional layer, a third dense connection block and a fourth dense connection block; and the third processing unit is specifically configured to:

perform tensor decomposition on a convolution kernel of the convolutional layer of the classifier to obtain a sixth tensor;

convolve the second respiratory infrared image sequence with the sixth tensor to obtain a fourth feature image;

perform tensor decomposition on a convolution kernel of the third dense connection block of the classifier to obtain a seventh tensor;

convolve the fourth feature image with the seventh tensor to obtain a fifth feature image;

process the fifth feature image by using the second-order pooling block of the classifier to obtain a sixth feature image;

perform tensor decomposition on a convolution kernel of the fourth dense connection block of the classifier to obtain an eighth tensor;

convolve the sixth feature image with the eighth tensor to obtain a seventh feature image;

perform tensor decomposition on weights of the full connection block of the classifier to obtain a ninth tensor;

obtain the third respiratory infrared image sequence according to the seventh feature image and the ninth tensor;

among them, the fourth feature image, the fifth feature image, the sixth feature image and the seventh feature image are all feature images of the second respiratory infrared image sequence.

Optionally, the classifier further includes a third transition layer and a fourth transition layer, and the third transition layer and the fourth transition layer are both 1×1×1 convolution kernels; the third transition layer is located between the second-order pooling block and the fourth dense connection block of the classifier to reduce the number of the sixth feature image; and the fourth transition layer is located between the fourth dense connection block and the full connection layer of the classifier to reduce the number of the seventh feature image.

The sleep quality evaluation system provided by the embodiments of the present application may be applied to the first embodiment and the second embodiment of the foregoing method, the details of which refer to the description of the first embodiment and the second embodiment of the foregoing method and will not be repeated herein again.

Figure 5:
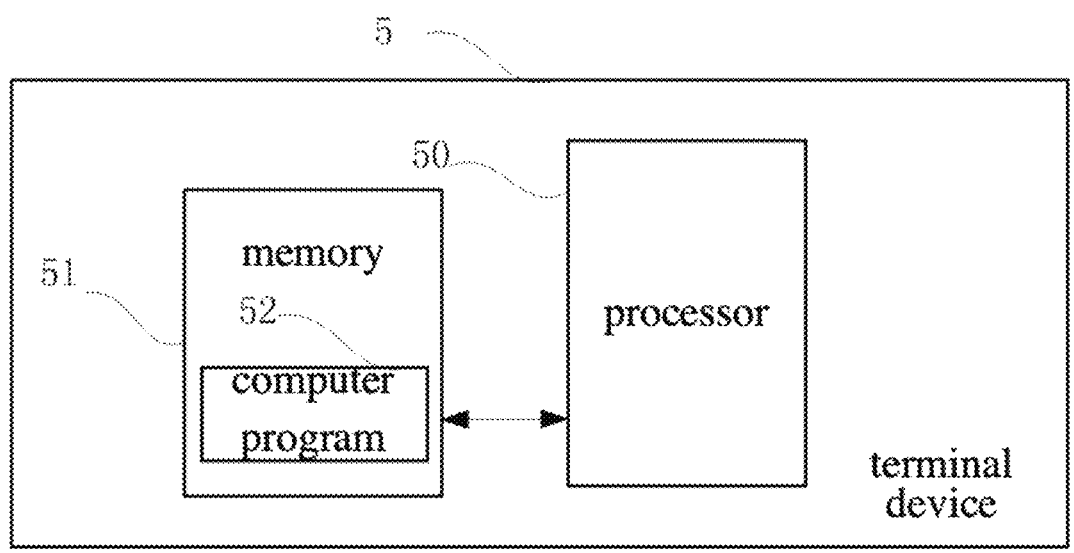
FIG. 5 is a schematic structural diagram of a terminal device provided by a fourth embodiment of the present application.

FIG. 5 is a schematic diagram of a terminal device provided by a fourth embodiment of the present application. As shown in FIG. 5, the terminal device 5 of this embodiment includes a processor 50, a memory 51, and a computer program 52 stored in the memory 51 and executable on the processor 50. The processor 50, when executing the computer program 52, implements steps in the embodiments of the foregoing sleep quality evaluation methods. Alternatively, the processor 50, when executing the computer program 52, implements functions of the modules/units in the embodiments of the foregoing systems.

The terminal device 5 may be a computing device such as a desktop computer, a notebook, a palmtop computer, or a cloud server etc. The terminal device may include, but is not limited to, a processor 50 and a memory 51. Those skilled in the art can understand that FIG. 5 is only an example of the terminal device 5 and does not constitute a limitation on the terminal device 5, which may include more or less components than those shown in the figure, or include a combination of certain components, or include different components. For example, the terminal device may also include an input and output device, a network access device, a bus, and so on.

The so-called processor 50 may be a CPU (Central Processing Unit), or may be other general-purpose processor, DSP (Digital Signal Processor), ASIC (Application Specific Integrated Circuit), FPGA (Field-Programmable Gate Array), or other programmable logic device, discrete gate or transistor logic device, discrete hardware component, etc. The general-purpose processor may be a microprocessor or the processor may also be any conventional processor or the like.

The memory 51 may be an internal storage unit of the terminal device 5, such as a hard disk or a storage of the terminal device 5. The memory 51 may also be an external storage device of the terminal device 5, such as a plug-in hard disk, a SMC (Smart Media Card,), or a SD (Secure Digital) card, flash card, etc. equipped on the terminal device 5. Further, the memory 51 may also include both an internal storage unit of the terminal device 5 and an external storage device. The memory 51 is used to store the computer program and other programs and data required by the terminal device. The memory 51 may also be used to temporarily store data that has been output or will be output.

It will be clearly understood by those skilled in the art that, for convenience and brevity of description, the division of the various functional units and modules described above is only exemplified. In practical applications, the above functions may be completed through assigning them to different functional units and modules according to needs. That is, the internal structure of the apparatus is divided into different functional units or modules to perform all or part of the functions described above. The various functional units and modules in the embodiments may be integrated into one processing unit, or each of the units may exist physically separately, or two or more units may be integrated into one unit. The above integrated unit may be implemented in a form of hardware, or may be implemented in a form of software functional module. Additionally, the specific names of the respective functional units and modules are only for the purpose of facilitating mutual differentiation, and are not intended to limit the protection scope of the present application. Regarding the specific implementation processes of the units and modules of the foregoing system, reference may be made to the corresponding processes of the foregoing method embodiments, and details of which will be not repeated herein again.

In the above embodiments, each of the embodiments is described with particular emphasis, and parts that are not detailed or described in a certain embodiment may refer to related description of other embodiments.

Those of ordinary skill in the art will appreciate that, the exemplary units and algorithm steps described in combination with the embodiments disclosed herein may be implemented by electronic hardware, or a combination of computer software and an electronic hardware. Whether these functions are performed in hardware or software depends on a specific application and a design constraint of the technical solution. A person skilled in the art may uses different methods to implement the described functions for each particular application, and such implementation should not be considered to be beyond the scope of the present application.

In the embodiments provided by the present application, it should be understood that the disclosed system/terminal device and method may be implemented in other manners. For example, the embodiments of the system/terminal device described above are merely illustrative. For example, the division of the modules or units is only a division of logical functions, and there may be other division manners in an actual implementation, for example, a plurality of units or components may be combined or integrated into another system, or some features may be ignored or not executed. Additionally, the mutual coupling or direct coupling or communication connection as shown or discussed may be indirect coupling or communication connection through some interfaces, apparatuses or units, which may be an electrical or mechanical form, or may be in other forms.

The units described as separate components may or may not be physically separate. The components displayed as units may or may not be physical units, that is, may be located in one place, or may be distributed to a plurality of network units. Some or all of the units may be selected according to actual needs to achieve the purpose of the solutions of the embodiments.

Additionally, the various functional units in the embodiments of the present application may be integrated into one processing unit, or each of the units may exist physically separately, or two or more units may be integrated into one unit. The above integrated unit may be implemented in a form of hardware, or may be implemented in a form of software functional module.

The integrated module/unit, if implemented in the form of the software functional unit and sold or used as a stand-alone product, may be stored in a computer-readable storage medium. Based on such understanding, the present application may implement all or part of the processes in the above embodiments through commanding related hardware by a computer program, and the computer program may be stored in the computer-readable storage medium. The computer program, when executed by a processor, may implement the steps of the various method embodiments described above. Among them, the computer program includes a computer program code, and the computer program code may be in a form of a source code, an object code, an executable file, or some intermediate forms etc. The computer-readable medium may include: any entity or apparatus capable of carrying the computer program code, a recording medium, a USB flash disk, a removable hard disk, a magnetic disk, an optical disk, a computer memory, a ROM (Read-Only Memory), a RAM (Random Access Memory), an electrical carrier signal, a telecommunication signal, or software distribution media or the like. It should be noted that, the content contained in the computer-readable medium may be appropriately added or removed according to requirements of legislation and patent practice in a jurisdiction. For example, in some jurisdictions, according to the legislation and the patent practice, the computer-readable medium does not include the electrical carrier signal and telecommunication signal.

The present application may implement all or part of the processes in the above-mentioned method embodiments through a computer program product. When the computer program product runs on a terminal device, causes the terminal device to realize steps of each of the method embodiments when executed.

The above embodiments are only used to illustrate, but are not intended to limit, the technical solutions of the present application; although the present application has been described in detail with reference to the foregoing embodiments, those of ordinary skill in the art should understand that the technical solutions disclosed in the above embodiments may still be modified, or some of the technical features therein may be equivalently replaced; and these modifications or replacements do not depart the essence of corresponding technical solutions from the spirit and scope of the technical solutions of the embodiments of the present application, and should be included in the protection scope of the present application.

What is claimed is:

1. A sleep quality evaluation method based on infrared image sequences, comprising:
   obtaining a plurality of respiratory infrared image sequences to be evaluated, wherein each of the plurality of respiratory infrared image sequences to be evaluated comprises a plurality of respiratory infrared image frames to be evaluated;
   performing sleep quality evaluation on each of the plurality of respiratory infrared image sequences to be evaluated by a classifier to obtain a-sleep quality evaluation results corresponding to the plurality of respiratory infrared image sequences to be evaluated;
   counting different sleep quality evaluation results according to the sleep quality evaluation results respectively corresponding to the plurality of respiratory infrared image sequences to be evaluated, and determining one sleep quality evaluation result accounting for a largest number in the different sleep quality evaluation results as a sleep quality evaluation result of a user, wherein before the performing the sleep quality evaluation on each of the plurality of respiratory infrared image sequences to be evaluated by the classifier, the sleep quality evaluation method further comprises:

training the classifier through a tensorized ternary generative adversarial network; and wherein the tensorized ternary generative adversarial network comprises a generator, the classifier and a discriminator; and the training the classifier through the tensorized ternary generative adversarial network comprises:

inputting one-dimensional random noise and a target label into the generator, and obtaining a first respiratory infrared image sequence carrying the target label through a tensor decomposition-based deconvolutional layer of the generator;

inputting the first respiratory infrared image sequence into the discriminator, and obtaining a discrimination result of the first respiratory infrared image sequence by the discriminator through a tensor decomposition-based network layer and a full connection layer of the discriminator;

training the generator according to the discrimination result;

acquiring an unlabeled second respiratory infrared image sequence;

inputting the unlabeled second respiratory infrared image sequence into the classifier, and acquiring a third respiratory infrared image sequence through a second-order pooling block, the tensor decomposition-based network layer and the full connection layer of the classifier, wherein the third respiratory infrared image sequence refers to a labeled second respiratory infrared image sequence;

acquiring a labeled fourth respiratory infrared image sequence;

training the discriminator according to the first respiratory infrared image sequence, the third respiratory infrared image sequence and the labeled fourth respiratory infrared image sequence, and acquiring a discrimination result of the third respiratory infrared image sequence by the discriminator; and training the classifier according to the first respiratory infrared image sequence, the discrimination result of the third respiratory infrared image sequence by the discriminator and the fourth respiratory infrared image sequence.

2. The sleep quality evaluation method of claim 1, wherein the performing the sleep quality evaluation on each of the plurality of respiratory infrared image sequences to be evaluated by the classifier to obtain the sleep quality evaluation results corresponding to the plurality of respiratory infrared image sequences to be evaluated comprises:

inputting each of the plurality of respiratory infrared image sequences to be evaluated into the classifier;

acquiring a target feature image of each of the plurality of respiratory infrared image sequences to be evaluated according to a second-order pooling block and a tensor decomposition-based network layer of the classifier;

performing the sleep quality evaluation on each of the plurality of respiratory infrared image sequences to be evaluated according to the target feature image and a tensor decomposition-based full connection layer of the classifier to obtain the sleep quality evaluation results corresponding to the plurality of respiratory infrared image sequences to be evaluated.

3. The sleep quality evaluation method of claim 1, wherein the obtaining the first respiratory infrared image sequence carrying the target label through the tensor decomposition-based deconvolutional layer of the generator comprises:

performing tensor decomposition on a deconvolution kernel of the deconvolutional layer of the generator to obtain a first tensor; and performing deconvolution calculation on the one-dimensional random noise and the first tensor to obtain the first respiratory infrared image sequence carrying the target label.

4. The sleep quality evaluation method of claim 1, wherein the tensor decomposition-based network layer of the discriminator comprises a tensor decomposition-based convolutional layer, a first dense connection block and a second dense connection block; and the obtaining the discrimination result of the first respiratory infrared image sequence by the discriminator through the tensor decomposition-based network layer and the full connection layer of the discriminator comprises:

performing tensor decomposition on a convolution kernel of the convolutional layer of the discriminator to obtain a second tensor;

convolving the first respiratory infrared image sequence with the second tensor to obtain a first feature image;

performing tensor decomposition on a convolution kernel of the first dense connection block of the discriminator to obtain a third tensor;

convolving the first feature image with the third tensor to obtain a second feature image;

performing tensor decomposition on a convolution kernel of the second dense connection block of the discriminator to obtain a fourth tensor;

convolving the second feature image with the fourth tensor to obtain a third feature image;

performing tensor decomposition on weights of the full connection layer of the discriminator to obtain a fifth tensor; and obtaining the discrimination result of the first respiratory infrared image sequence by the discriminator according to the third feature image and the fifth tensor;

wherein the first feature image, the second feature image and the third feature image are all feature images of the first respiratory infrared image sequence.

5. The sleep quality evaluation method of claim 4, wherein the discriminator further comprises a first transition layer and a second transition layer, the first transition layer and the second transition layer are both 1×1×1 convolution kernels; the first transition layer is located between the first dense connection block and the second dense connection block of the discriminator to reduce a number of the second feature image; the second transition layer is located between the second dense connection block and a full connection block of the discriminator to reduce a number of the third feature image.

6. The sleep quality evaluation method of claim 1, wherein the tensor decomposition-based network layer of the classifier comprises a tensor decomposition-based convolutional layer, a third dense connection block and a fourth dense connection block; and the acquiring the third respiratory infrared image sequence through the second-order pooling block, the tensor decomposition-based network layer and the full connection layer of the classifier comprises:

performing tensor decomposition on a convolution kernel of the convolutional layer of the classifier to obtain a sixth tensor;

convolving the unlabeled second respiratory infrared image sequence with the sixth tensor to obtain a fourth feature image;

performing tensor decomposition on a convolution kernel of the third dense connection block of the classifier to obtain a seventh tensor;

convolving the fourth feature image with the seventh tensor to obtain a fifth feature image;

processing the fifth feature image by using the second-order pooling block of the classifier to obtain a sixth feature image;

performing tensor decomposition on a convolution kernel of the fourth dense connection block of the classifier to obtain an eighth tensor;

convolving the sixth feature image with the eighth tensor to obtain a seventh feature image;

performing tensor decomposition on weights of a full connection block of the classifier to obtain a ninth tensor; and obtaining the third respiratory infrared image sequence according to the seventh feature image and the ninth tensor;

wherein the fourth feature image, the fifth feature image, the sixth feature image and the seventh feature image are all feature images of the labeled second respiratory infrared image sequence.

7. The sleep quality evaluation method of claim 6, wherein the classifier further comprises a third transition layer and a fourth transition layer, and the third transition layer and the fourth transition layer are both 1×1×1 convolution kernels; the third transition layer is located between the second-order pooling block and the fourth dense connection block of the classifier to reduce a number of the sixth feature image; and the fourth transition layer is located between the fourth dense connection block and the full connection layer of the classifier to reduce a number of the seventh feature image.

8. A terminal device, comprising a memory, a processor and a computer program stored in the memory and executable on the processor, wherein the processor, when executing the computer program, implements operations that comprise:

obtaining a plurality of respiratory infrared image sequences to be evaluated, wherein each of the plurality of respiratory infrared image sequences to be evaluated comprises a plurality of respiratory infrared image frames to be evaluated;

performing sleep quality evaluation on each of the plurality of respiratory infrared image sequences to be evaluated by a classifier to obtain sleep quality evaluation results corresponding to the plurality of respiratory infrared image sequences to be evaluated;

counting different sleep quality evaluation results according to the sleep quality evaluation results respectively corresponding to the plurality of respiratory infrared image sequences to be evaluated, and determining one sleep quality evaluation result accounting for a largest number in the different sleep quality evaluation results as a sleep quality evaluation result of a user, wherein before the performing the sleep quality evaluation on each of the plurality of respiratory infrared image sequences to be evaluated by the classifier, the operations implemented by the processor further comprise:

training the classifier through a tensorized ternary generative adversarial network, and wherein the tensorized ternary generative adversarial network comprises a generator, the classifier and a discriminator; and the training the classifier through the tensorized ternary generative adversarial network comprises:

inputting one-dimensional random noise and a target label into the generator, and obtaining a first respiratory infrared image sequence carrying the target label through a tensor decomposition-based deconvolutional layer of the generator;

inputting the first respiratory infrared image sequence into the discriminator, and obtaining a discrimination result of the first respiratory infrared image sequence by the discriminator through a tensor decomposition-based network layer and a full connection layer of the discriminator;

training the generator according to the discrimination result;

acquiring an unlabeled second respiratory infrared image sequence;

inputting the unlabeled second respiratory infrared image sequence into the classifier, and acquiring a third respiratory infrared image sequence through a second-order pooling block, the tensor decomposition-based network layer and the full connection layer of the classifier, wherein the third respiratory infrared image sequence refers to a labeled second respiratory infrared image sequence;

acquiring a labeled fourth respiratory infrared image sequence;

training the discriminator according to the first respiratory infrared image sequence, the third respiratory infrared image sequence and the labeled fourth respiratory infrared image sequence, and acquiring a discrimination result of the third respiratory infrared image sequence by the discriminator; and training the classifier according to the first respiratory infrared image sequence, the discrimination result of the third respiratory infrared image sequence by the discriminator and the fourth respiratory infrared image sequence.

9. The terminal device of claim 8, wherein the performing the sleep quality evaluation on each of the plurality of respiratory infrared image sequences to be evaluated by the classifier to obtain the sleep quality evaluation results corresponding to the plurality of respiratory infrared image sequences to be evaluated comprises:

inputting each of the plurality of respiratory infrared image sequences to be evaluated into the classifier;

acquiring a target feature image of each of the plurality of respiratory infrared image sequences to be evaluated according to a second-order pooling block and a tensor decomposition-based network layer of the classifier; and performing the sleep quality evaluation on each of the plurality of respiratory infrared image sequences to be evaluated according to the target feature image and a tensor decomposition-based full connection layer of the classifier to obtain the sleep quality evaluation results corresponding to the plurality of respiratory infrared image sequences to be evaluated.

10. The terminal device of claim 8, wherein the obtaining the first respiratory infrared image sequence carrying the target label through the tensor decomposition-based deconvolutional layer of the generator comprises:

performing tensor decomposition on a deconvolution kernel of the deconvolutional layer of the generator to obtain a first tensor; and
performing deconvolution calculation on the one-dimensional random noise and the first tensor to obtain the first respiratory infrared image sequence carrying the target label.

11. The terminal device of claim 8, wherein the tensor decomposition-based network layer of the discriminator comprises a tensor decomposition-based convolutional layer, a first dense connection block and a second dense connection block; and the obtaining the discrimination result of the first respiratory infrared image sequence by the discriminator through the tensor decomposition-based network layer and the full connection layer of the discriminator comprises:
performing tensor decomposition on a convolution kernel of the convolutional layer of the discriminator to obtain a second tensor;
convolving the first respiratory infrared image sequence with the second tensor to obtain a first feature image;
performing tensor decomposition on a convolution kernel of the first dense connection block of the discriminator to obtain a third tensor;
convolving the first feature image with the third tensor to obtain a second feature image;
performing tensor decomposition on a convolution kernel of the second dense connection block of the discriminator to obtain a fourth tensor;
convolving the second feature image with the fourth tensor to obtain a third feature image;
performing tensor decomposition on weights of the full connection layer of the discriminator to obtain a fifth tensor; and
obtaining the discrimination result of the first respiratory infrared image sequence by the discriminator according to the third feature image and the fifth tensor;
wherein the first feature image, the second feature image and the third feature image are all feature images of the first respiratory infrared image sequence.

12. The terminal device of claim 11, wherein the discriminator further comprises a first transition layer and a second transition layer, the first transition layer and the second transition layer are both 1×1×1 convolution kernels; the first transition layer is located between the first dense connection block and the second dense connection block of the discriminator to reduce a number of the second feature image; the second transition layer is located between the second dense connection block and a full connection block of the discriminator to reduce a number of the third feature image.

13. The terminal device of claim 8, wherein the tensor decomposition-based network layer of the classifier comprises a tensor decomposition-based convolutional layer, a third dense connection block and a fourth dense connection block; and the acquiring the third respiratory infrared image sequence through the second-order pooling block, the tensor decomposition-based network layer and the full connection layer of the classifier comprises:
performing tensor decomposition on a convolution kernel of the convolutional layer of the classifier to obtain a sixth tensor;
convolving the unlabeled second respiratory infrared image sequence with the sixth tensor to obtain a fourth feature image;
performing tensor decomposition on a convolution kernel of the third dense connection block of the classifier to obtain a seventh tensor;
convolving the fourth feature image with the seventh tensor to obtain a fifth feature image;
processing the fifth feature image by using the second-order pooling block of the classifier to obtain a sixth feature image;
performing tensor decomposition on a convolution kernel of the fourth dense connection block of the classifier to obtain an eighth tensor;
convolving the sixth feature image with the eighth tensor to obtain a seventh feature image;
performing tensor decomposition on weights of a full connection block of the classifier to obtain a ninth tensor; and
obtaining the third respiratory infrared image sequence according to the seventh feature image and the ninth tensor;
wherein the fourth feature image, the fifth feature image, the sixth feature image and the seventh feature image are all feature images of the labeled second respiratory infrared image sequence.

14. The terminal device of claim 13, wherein the classifier further comprises a third transition layer and a fourth transition layer, and the third transition layer and the fourth transition layer are both 1×1×1 convolution kernels; the third transition layer is located between the second-order pooling block and the fourth dense connection block of the classifier to reduce a number of the sixth feature image; and the fourth transition layer is located between the fourth dense connection block and the full connection layer of the classifier to reduce a number of the seventh feature image.

15. A non-transitory computer-readable storage medium storing a computer program thereon, wherein the computer program, when executed by a processor, causes the processor to implement operations that comprise:
obtaining a plurality of respiratory infrared image sequences to be evaluated,
wherein each of the plurality of respiratory infrared image sequences to be evaluated comprises a plurality of respiratory infrared image frames to be evaluated;
performing sleep quality evaluation on each of the plurality of respiratory infrared image sequences to be evaluated by a classifier to obtain sleep quality evaluation results corresponding to the plurality of respiratory infrared image sequences to be evaluated;
counting different sleep quality evaluation results according to the sleep quality evaluation results respectively corresponding to the plurality of respiratory infrared image sequences to be evaluated, and determining one sleep quality evaluation result accounting for a largest number in the different sleep quality evaluation results as a sleep quality evaluation result of a user,
wherein before the performing the sleep quality evaluation on each of the plurality of respiratory infrared image sequences to be evaluated by the classifier, the operations implemented by the processor further comprise:
training the classifier through a tensorized ternary generative adversarial network; and
wherein the tensorized ternary generative adversarial network comprises a generator, the classifier and a discriminator; and the training the classifier through the tensorized ternary generative adversarial network comprises:
inputting one-dimensional random noise and a target label into the generator, and obtaining a first respiratory infrared image sequence carrying the target label through a tensor decomposition-based deconvolutional layer of the generator;

inputting the first respiratory infrared image sequence into the discriminator, and obtaining a discrimination result of the first respiratory infrared image sequence by the discriminator through a tensor decomposition-based network layer and a full connection layer of the discriminator;

training the generator according to the discrimination result;

acquiring an unlabeled second respiratory infrared image sequence;

inputting the unlabeled second respiratory infrared image sequence into the classifier, and acquiring a third respiratory infrared image sequence through a second-order pooling block, the tensor decomposition-based network layer and the full connection layer of the classifier, wherein the third respiratory infrared image sequence refers to a labeled second respiratory infrared image sequence;

acquiring a labeled fourth respiratory infrared image sequence;

training the discriminator according to the first respiratory infrared image sequence, the third respiratory infrared image sequence and the labeled fourth respiratory infrared image sequence, and acquiring a discrimination result of the third respiratory infrared image sequence by the discriminator; and training the classifier according to the first respiratory infrared image sequence, the discrimination result of the third respiratory infrared image sequence by the discriminator and the fourth respiratory infrared image sequence.

16. The non-transitory computer-readable storage medium of claim 15, wherein the performing the sleep quality evaluation on each of the plurality of respiratory infrared image sequences to be evaluated by the classifier to obtain the sleep quality evaluation results corresponding to the plurality of respiratory infrared image sequences to be evaluated comprises:

inputting each of the plurality of respiratory infrared image sequences to be evaluated into the classifier;

acquiring a target feature image of each of the plurality of respiratory infrared image sequences to be evaluated according to a second-order pooling block and a tensor decomposition-based network layer of the classifier; and performing the sleep quality evaluation on each of the plurality of respiratory infrared image sequences to be evaluated according to the target feature image and a tensor decomposition-based full connection layer of the classifier to obtain the sleep quality evaluation results corresponding to the plurality of respiratory infrared image sequences to be evaluated.

17. The non-transitory computer-readable storage medium of claim 15, wherein the obtaining the first respiratory infrared image sequence carrying the target label through the tensor decomposition-based deconvolutional layer of the generator comprises:

performing tensor decomposition on a deconvolution kernel of the deconvolutional layer of the generator to obtain a first tensor; and performing deconvolution calculation on the one-dimensional random noise and the first tensor to obtain the first respiratory infrared image sequence carrying the target label.

18. The non-transitory computer-readable storage medium of claim 15, wherein the tensor decomposition-based network layer of the discriminator comprises a tensor decomposition-based convolutional layer, a first dense connection block and a second dense connection block; and the obtaining the discrimination result of the first respiratory infrared image sequence by the discriminator through the tensor decomposition-based network layer and the full connection layer of the discriminator comprises:

performing tensor decomposition on a convolution kernel of the convolutional layer of the discriminator to obtain a second tensor;

convolving the first respiratory infrared image sequence with the second tensor to obtain a first feature image;

performing tensor decomposition on a convolution kernel of the first dense connection block of the discriminator to obtain a third tensor;

convolving the first feature image with the third tensor to obtain a second feature image;

performing tensor decomposition on a convolution kernel of the second dense connection block of the discriminator to obtain a fourth tensor;

convolving the second feature image with the fourth tensor to obtain a third feature image;

performing tensor decomposition on weights of the full connection layer of the discriminator to obtain a fifth tensor; and obtaining the discrimination result of the first respiratory infrared image sequence by the discriminator according to the third feature image and the fifth tensor;

wherein the first feature image, the second feature image and the third feature image are all feature images of the first respiratory infrared image sequence.

19. The non-transitory computer-readable storage medium of claim 18, wherein the discriminator further comprises a first transition layer and a second transition layer, the first transition layer and the second transition layer are both 1×1×1 convolution kernels; the first transition layer is located between the first dense connection block and the second dense connection block of the discriminator to reduce a number of the second feature image; the second transition layer is located between the second dense connection block and a full connection block of the discriminator to reduce a number of the third feature image.

20. The non-transitory computer-readable storage medium of claim 15, wherein the tensor decomposition-based network layer of the classifier comprises a tensor decomposition-based convolutional layer, a third dense connection block and a fourth dense connection block; and the acquiring the third respiratory infrared image sequence through the second-order pooling block, the tensor decomposition-based network layer and the full connection layer of the classifier comprises:

performing tensor decomposition on a convolution kernel of the convolutional layer of the classifier to obtain a sixth tensor;

convolving the unlabeled second respiratory infrared image sequence with the sixth tensor to obtain a fourth feature image;

performing tensor decomposition on a convolution kernel of the third dense connection block of the classifier to obtain a seventh tensor;

convolving the fourth feature image with the seventh tensor to obtain a fifth feature image;

processing the fifth feature image by using the second-order pooling block of the classifier to obtain a sixth feature image;

performing tensor decomposition on a convolution kernel of the fourth dense connection block of the classifier to obtain an eighth tensor;

convolving the sixth feature image with the eighth tensor to obtain a seventh feature image;

performing tensor decomposition on weights of a full connection block of the classifier to obtain a ninth tensor; and obtaining the third respiratory infrared image sequence according to the seventh feature image and the ninth tensor;

wherein the fourth feature image, the fifth feature image, the sixth feature image and the seventh feature image are all feature images of the labeled second respiratory infrared image sequence.

* * * * *